United States Patent
Rossen et al.

(10) Patent No.: US 7,045,640 B2
(45) Date of Patent: May 16, 2006

(54) METHOD OF PRODUCING 5-FORMYL-2-FURYLBORONIC ACID

(75) Inventors: Kai Rossen, Hanau (DE); Milan Latinovic, Nidda (DE); Martin Sarich, Alzenau (DE); Peter Gardner, Stockton-on-Tees (GB); Simon Rowell, Brompton (GB)

(73) Assignee: Degussa AG, Duesseldorf (DE)

( * ) Notice: Subject to any disclaimer, the term of this patent is extended or adjusted under 35 U.S.C. 154(b) by 164 days.

(21) Appl. No.: 10/663,798

(22) Filed: Sep. 17, 2003

(65) Prior Publication Data

US 2004/0127725 A1 Jul. 1, 2004

(30) Foreign Application Priority Data

Sep. 25, 2002 (EP) .................. 02021439

(51) Int. Cl.
*C07D 307/56* (2006.01)
(52) U.S. Cl. ..................................... 549/213
(58) Field of Classification Search ................. 549/213
See application file for complete search history.

(56) References Cited

FOREIGN PATENT DOCUMENTS

WO            96/16046    *  5/1996

OTHER PUBLICATIONS

P. R. Parry, et al., Organic & Biomolecular Chemistry, vol. 1, No. 9, pp. 1447-1449, XP-002256394, "5-Formyl-2-Furylboronic Acid as a Versatile Bifunctional Reagent for the Synthesis of π-Extended Heteroarylfuran Systems", May 7, 2003.

D. Florentin, et al., Bulletin de la Societe Chimique de France, No. 11/12, pp. 1999-2005, XP-009018458, "Synthèse et Étude RMN Des Acides Furanneboroniques et Formylfuranneboroniques", 1976.

M. S. McClure, et al., Synthesis, No. 11, pp. 1681-1685, XP-001155250, "A Practical One-Pot Synthesis of 5-Aryl-2-Furaldehydes", 2001.

* cited by examiner

*Primary Examiner*—Taofiq Solola
(74) *Attorney, Agent, or Firm*—Oblon, Spivak, McClelland, Maier & Neustadt, P.C.

(57) ABSTRACT

5-formyl-2-furylboronic acid is produced by a) adding a base to a composition containing a boric acid ester and 2-furaldehyde, thereby obtaining a reaction mixture and protecting the formyl group of said 2-furaldehyde with a protective group, b) working-up of the reaction mixture in an acidic medium, and c) isolating of the 5-formyl-2-furylboronic acid.

19 Claims, No Drawings ure_group and an N,O-acetal protective group. In case
METHOD OF PRODUCING 5-FORMYL-2-FURYLBORONIC ACID

BACKGROUND OF THE INVENTION

1. Field of the Invention

The present invention refers to an improved method of producing 5-formyl-2-furylboronic acid.

2. Discussion of the Background

The Suzuki coupling reaction is a well known method for the formation of aryl-aryl bonds, whereby an aryl borate is reacted with an aryl halide in a palladium catalyzed coupling reaction. The Suzuki coupling reaction is very useful in the synthesis of drugs and consequently it is under current investigation to provide suitable starting materials.

One very useful building block is 5-formyl-2-furylboronic acid. Florentin et al. (Bull. Soc. Chim. Fr. 1976, 11–12, 1999) discloses the preparation of 5-formyl-2-furylboronic acid starting from 2-furaldehyde. The formyl functionality of the 2-furaldehyde is protected as diethylacetal and said diethylacetal is metalated with methyllithium. The obtained lithiated furan is subsequently reacted with tributyl borate and after acidic quench the 5-formyl-2-furylboronic acid was isolated. Florentin et al. investigated the $^1$H and $^{13}$C NMR spectra of said furylboronic acid. There is no further disclosure regarding the reaction conditions, yield or purity of the obtained 5-formyl-2-furylboronic acid.

In an earlier paper, Florentin et al. (C.R.Acad.Sc.Paris, Ser. C 1970, 270, 1608) describes the preparation of 5-formyl-2-furylboronic acid by metalation of 2-formyl-5-bromofuran with butyl lithium and subsequent reaction of the metalated furan derivative with n-butylborate. After acidic work-up the 5-formnyl-2-furylboronic acid was obtained as white crystals in a 15% yield.

WO96/16046 describes the synthesis of 5-formyl-2-furylboronic acid whereby furfuraldiethylacetal is metalated with butyl lithium in ether as a solvent at a temperature of –40° C. The reaction mixture is stirred at room temperature for additional 2 hours and subsequently again chilled to –40° C. A solution of trimethylborate in ether is added and subsequently heated to room temperature and then held at reflux. After acidic work-up and recrystallization 5-formyl-2-furylboronic acid was isolated as a colorless solid in 26% yield.

McClure (Synthesis 2001, No.11, 1681–1685) describes a practical one-pot synthesis of 5-aryl-2-furaldehyde via palladium mediated Suzuki coupling of arylhalides with in situ generated 5-(diethoxymethyl)-2-furylboronic acid. 5-(Diethoxymethyl)-2-furylboronic acid is used as building block because 5-formyl-2-furylboronic acid is considered to be cost-prohibitive and the described preparation methods of same suffer from low temperature requirements, capricious reproducibility, tedious work-up as well as unsuitably low purity and isolated yields. McClure was not able to improve the isolation of 5-(diethoxymethyl)-2-furylboronic acid as well as 5-formyl-2-furylboronic acid and therefore decided to use a crude solution of 5-(diethoxymethyl)-2-furylboronic acid in the subsequent Suzuki coupling.

Roschangar et al. (Tetrahedron 58 (2002) 1657–1666) describes the preparation of 5-formyl-2-furylboronic acid, whereby starting from furfural said boronic acid is obtained via metalation and subsequent addition of triisopropylborate to the metalated furan derivative. Because of the difficulties described in the prior art like low temperature requirements, capricious reproducibility, tedious workup as well as unsuitably low purity and isolated yields Roschangar et al. did not try to isolate 5-formyl-2-furylboronic acid. Therefore, they applied the boronic acid to a subsequent Suzuki coupling without further purification. 5-Formyl-2-furylboronic acid was obtained as crude reaction solution, only.

SUMMARY OF THE INVENTION

It is an object of the present invention to provide a method of producing 5-formyl-2-furylboronic acid with improved yield, stability and purity of the obtained 5-formyl-2-furylboronic acid. A further object of the present invention is to improve and optimize the reaction conditions for preparing said boronic acid.

This and other objects have been achieved by the present invention the first embodiment of which includes a method of producing 5-formyl-2-furylboronic acid, comprising:

a) adding a base to a composition comprising a boric acid ester and 2-furaldehyde, thereby obtaining a reaction mixture and protecting the formyl group of said 2-furaldehyde with a protective group, b) working-up of said reaction mixture in an acidic medium, and c) isolating 5-formyl-2-furylboronic acid.

DETAILED DESCRIPTION OF THE INVENTION

The technical problem of the present invention is solved by a method of producing 5-formyl-2-furylboronic acid comprising:

a) addition of a base to a composition comprising a boric acid ester and 2-furaldehyde whereby the formyl functionality of the 2-furaldehyde is protected with a protective group, and b) acidic work-up of the reaction mixture of step a), and c) isolation of 5-formyl-2-furylboronic acid.

The following reaction scheme exhibits the method of producing of 5-formyl-2-furylboronic acid (1).

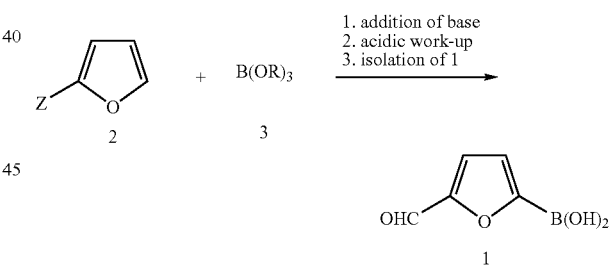

A base is added to a mixture comprising a protected 2-furaldehyde (2) and a boric acid ester (3). In the protected 2-furaldehyde (2), Z is the formyl functionality which is protected with a suitable protective group. In boric acid ester (3), R is a suitable residue such as a linear or branched alkyl group or an aryl group which is optionally substituted with an alkyl group.

In a preferred embodiment the boric acid ester of step a) is an alkylboric acid ester and/or arylboric acid ester. The alkylboric acid ester of step a) is preferable selected from the group consisting of $B(OiPr)_3$, $B(OEt)_3$, $B(OMe)_3$, $B(OPr)_3$, $B(OBu)_3$, and mixtures thereof.

The protective group for protecting the formyl functionality of the 2-furaldehyde may be any protective group that is known to a person skilled in the art to be suitable. In a preferred embodiment the protective group is an O,O-acetal protective group or an N,O-acetal protective group. In case that the acetal protective group is an O,O-acetal protective group preferably the alcohol is selected from the group consisting of alkanols having 1 to 10 carbon atoms, alkandiols having 1 to 20 carbon atoms, and mixtures thereof. In a preferred embodiment the protective group is selected from methanol, ethanol, propanol, butanol, ethylene glycol, 1,3-propane diol, and N-substituted ethanol amines.

In a preferred embodiment the base of step a) is selected from the group consisting of alkyl metal, metal amides, and mixtures thereof. Preferably the alkyl metal is alkyl lithium, alkyl sodium or alkyl potassium. In a further preferred embodiment the base of step a) is selected from the group consisting of lithium hexamethyldisilazane, sodium hexamethyldisilazane, potassium hexamethyldisilazane, lithium diisopropylamide, butyl lithium, methyl lithium, ethyl lithium, propyl lithium, and mixtures thereof.

It is preferred that a solvent is present in step a). The solvent can be every solvent that is customary to a person skilled in the art, such as a solvent selected from the group consisting of tetrahydrofuran, 1,2-dimethoxyethane, 1,4-dioxane, and mixtures thereof.

The addition of a base to a composition comprising a boric ester and the protected 2-furaldehyde may be carried out at a temperature of from −100° C. to 30° C., preferably −78° C. to 5° C., even more preferred from −30° C. to 0° C., and most preferred from −20° C. to 0° C., and −10° C. to 0° C. The temperature includes all values and subvalues therebetween, especially including −90, −80, −70, −60, −50, −40, −30, −20, −10, 0, 10 and 20° C.

The ratio of the base to the protected 2-furaldehyde in step a) is preferably from 1.0 to 1.6 equivalents of base, preferably from 1.0 to 1.4 equivalents, even more preferred from 1.1 to 1.3 equivalents of base per mole protected 2-furaldehyde. The ratio of the base to the protected 2-furaldehyde in step a) includes all values and subvalues therebetween, especially including 1.1, 1.2, 1.3 and 1.4 moles.

The ratio of the boric acid ester to the protected 2-furaldehyde is from 1,0 to 1,8, even more preferred from 1,2 to 1,5 moles, and most preferred from 1,3 to 1,5 moles of boric acid ester per mole protected 2-furaldehyde. The ratio of the boric acid ester to the protected 2-furaldehyde includes all values and subvalues therebetween, especially including 1.1, 1.2, 1.3, 1.4, 1.5, 1.6 and 1.7 moles.

In a preferred embodiment the acidic work-up in step b) is conducted by using an aqueous acid. The aqueous acid can be any acid that is customary to a person skilled in the art. Preferably, the aqueous acid is selected from the group consisting of hydrochloric acid, sulfuric acid, citric acid, acetic acid, formic acid, and mixtures thereof.

The acidic work-up of the reaction mixture of step a) can either be carried out by addition of an acid to the reaction mixture of step a), or by addition of the reaction mixture of step a) to an acid.

The acidic work-up of step b) can be carried out at a temperature of from −10° C. to 70° C., preferably from 0° C. to 60° C., most preferred from 10° C. to 50° C. The temperature of step b) includes all values and subvalues therebetween, especially including −5, 0, 5, 10, 15, 20, 25, 30, 40, 50, and 60° C.

The isolation of 5-formyl-2-furylboronic acid of step c) can preferably be performed by means of filtration, centrifugation, and/or crystallization.

In a preferred embodiment the obtained 5-formyl-furanboronic acid of step c) is further purified by means of recrystallization. The recrystallization can be performed by using any suitable solvent. It is preferred that the solvent is a polar solvent, such as acetonitrile, water, and mixtures thereof.

In a preferred embodiment the method of producing 5-formyl-2-furylboronic acid comprises the steps of a) addition of lithium diisopropylamide to a composition comprising triisopropylborate and furfuraldiethylacetal and, optionally, a solvent, and b) acidic work-up of the reaction mixture of step a) and c) isolation of 5-formyl-2-furylboronic acid.

5-Formyl-2-furylboronic acid which is manufactured according to the teaching of the present invention is a white crystalline solid. The stability of the obtained 5-formyl-2-furylboronic acid is sufficient to employ said boronic acid as useful building-block to subsequent reactions in drug synthesis like the Suzuki coupling reaction. Furthermore, the reaction conditions and procedures are more convenient to a person skilled in the art and the reaction sequence is capable of providing a sufficient amount of 5-formyl-2-furylboronic acid.

Having generally described this invention, a further understanding can be obtained by reference to certain specific examples which are provided herein for purposes of illustration only, and are not intended to be limiting unless otherwise specified.

EXAMPLES

A dried 500 mL 3-neck flask with mechanical stirrer, internal thermometer and addition funnel under nitrogen was charged with 20,16 g (0,118 mol) furfuraldiethylacetal, 33,4 g (0,177 mol) triisopropylborate and 40 mL of anhydrous THF. The water content of the reaction mixture was measured according to the Karl-Fischer-titration method and was determined to be less than 800 μg/mL of water. The solution was cooled to an internal temperature of −10° C. Keeping the temperature at −10° C. to 0° C. 84 mL (25 wt %, 1.84 M solution THF, heptane, ethylbenzene from Chemmetal, content determined by titration, 1.3 equivalents) LDA was added via addition funnel to the reaction mixture over a period of 1 hour. Using a canula the reaction mixture was subsequently transferred to precooled aqueous hydrochloric acid which was obtained by mixing 33 mL of concentrated hydrochloric acid and 55 mL water. The reaction temperature was maintained at a temperature of less than 30° C. The resulting tan slurry of 5-formyl-2-furylboronic acid was cooled to 0° C. and filtered. The filter cake was washed twice with 20 mL of cold water to give 17.6 g of wet cake. Drying (40° C., vacuum oven) gave 12.41 g of an off-white product. The overall yield of 5-formyl-2-furylboronic acid was 75%. The content of unreacted furfural in the crude product was determined to be less than 0.1%.

Optional Recrystallization:

A 2 L neck flask with mechanical stirrer was charged with 130 g 5-formyl-2-furylboronic acid, 900 mL acetonitrile and 400 mL water. The resulting slurry was heated to reflux, at which point the solids were in solution. The dark solution was cooled overnight to 0° C. The resulting slurry was filtered and washed with 100 mL of acetonitrile. Drying gives 116.7 g of 5-formyl-2-furylboronic acid as a white crystalline solid (90% yield).

5-Formyl-2-furylboronic acid synthesized according to the method of the present invention was either with or without optional recrystallization stable at room temperature for more than one year. By way of contrast, 5-formyl-2-furylboronic acid synthesized according to methods known in the prior art decomposed spontaneously upon standing at room temperature within days or hours.

European patent application 02 021 439.1 filed Sep. 25, 2002, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A method of producing 5-formyl-2-furylboronic acid, comprising:
   a) reacting the formyl group of 2-furaldehyde with a protective group, to obtain a protected 2-furaldehyde;
   b) adding a base to a composition comprising a boric acid ester and said protected 2-furaldehyde, thereby obtaining a reaction mixture and reacting said protected 2-furaldehyde, said base and said boric acid ester;
   c) adding said reaction mixture to an acidic medium;
   d) obtaining 5-formyl-2-furylboronic acid from said acidic medium;
   wherein said base is an alkyl metal, metal amide or mixtures thereof.

2. The method according to claim 1, wherein said boric acid ester is an alkyl boric acid ester, aryl boric acid ester or a mixture thereof.

3. The method according to claim 2, wherein said alkyl boric acid ester is selected from the group consisting of $B(OiPr)_3$, $B(OEt)_3$, $B(OMe)_3$, $B(OPr)_3$, $B(OBu)_3$, and mixtures thereof.

4. The method according to claim 1, wherein said protective group is a O,O-acetal protective group or N,O-acetal protective group.

5. The method according to claim 4, wherein said acetal protective group is selected from the group consisting of alkanols having 1 to 10 carbon atoms, alkandiols having 1 to 20 carbon atoms, and mixtures thereof.

6. The method according to claim 1, wherein said base is selected from the group consisiting of lithium hexamethyldisilazane, sodium hexamethyldisilazane, potassium hexamethyldisilazane, lithium diisopropylamide, butyl lithium, methyl lithium, ethyl lithium, propyl lithium, and mixtures thereof.

7. The method according to claim 1, wherein a solvent is present in step a);
   wherein said solvent is selected from the group consisting of tetrahydrofuran, 1,2-dimethoxyethane, 1,4-dioxane, and mixtures thereof.

8. The method according to claim 1, wherein said working-up is conducted by using an aqueous acid.

9. The method according to claim 8, wherein said aqueous acid is selected from the group consisting of hydrochloric acid, sulfuric acid, citric acid, acetic acid, formic acid, and mixtures thereof.

10. The method according to claim 8, wherein said isolating of 5-formyl-furan-boronic acid is carried out by filtration, centrifugation, crystallization or combinations thereof.

11. The method according to claim 1, further comprising recrystallizing 5-formyl-furanboronic acid, thereby purifying said 5-formyl-furan-boronic acid.

12. The method according to claim 1, comprising:
   a) adding lithium diisopropylamide to a composition comprising triisopropylborate and furfuraldiethylacetal, and optionally a solvent, thereby obtaining said reaction mixture, and
   b) working-up of said reaction mixture in an acidic medium, and
   c) isolating 5-formyl-2-furylboronic acid.

13. The method according to claim 1, wherein said protective group is selected from the group consisting of methanol, ethanol, propanol, butanol, ethylene glycol, 1,3-propane diol, and N-substituted ethanol amines.

14. The method according to claim 1, wherein said alkyl metal is alkyl lithium, alkyl sodium or alkyl potassium.

15. The method according to claim 1, wherein said adding proceeds at a temperature of from −100° C. to 30° C.

16. The method according to claim 1, wherein a ratio of said base to the protected 2-furaldehyde in step a) is from 1.0 to 1.6 equivalents of base per mole protected 2-furaldehyde.

17. The method according to claim 1, wherein a ratio of the boric acid ester to the protected 2-furaldehyde is from 1,0 to 1,8 moles of boric acid ester per mole of protected 2-furaldehyde.

18. The method according to claim 1, wherein said working-up is carried out at a temperature of from −10° C. to 70° C.

19. A method of producing 5-formyl-2-furylboronic acid, comprising:
   a) reacting the formyl group of 2-furaldehyde with a protective group, to obtain a protected 2-furaldehyde;
   b) adding a base to a composition comprising a boric acid ester and said protected 2-furaldehyde, thereby obtaining a reaction mixture and reacting said protected 2-furaldehyde, said base and said boric acid ester;
   c) adding said reaction mixture to an acidic medium; and
   d) obtaining 5-formyl-2-furylboronic acid from said acidic medium;
   wherein said base is selected from the group consisiting of lithium hexamethyldisilazane, sodium hexamethyldisilazane, potassium hexamethyldisilazane, lithium diisopropylamide, butyl lithium, methyl lithium, ethyl lithium, propyl lithium, and mixtures thereof.

* * * * *